United States Patent [19]

Bucci et al.

[11] Patent Number: 4,584,130

[45] Date of Patent: Apr. 22, 1986

[54] INTRAMOLECULARLY CROSS-LINKED HEMOGLOBIN AND METHOD OF PREPARATION

[75] Inventors: Enrico Bucci; Clara Fronticelli-Bucci, both of Baltimore; Ramachandra Hosmane, Columbia, all of Md.

[73] Assignee: University of Maryland, Baltimore, Md.

[21] Appl. No.: 717,783

[22] Filed: Mar. 29, 1985

[51] Int. Cl.$^4$ .................. C07C 103/52; A61K 35/18; A61K 37/02; C07K 13/00
[52] U.S. Cl. .................. 260/112 B; 260/112.5 R; 260/115; 424/101; 514/6
[58] Field of Search ............ 260/112 B, 112.5 R, 260/115; 424/101; 514/6

[56] References Cited

U.S. PATENT DOCUMENTS

| | | | |
|---|---|---|---|
| 3,925,344 | 12/1975 | Mazur | 260/112.5 R |
| 4,001,200 | 1/1977 | Bonsen et al. | 260/112 B X |
| 4,001,401 | 1/1977 | Bonsen et al. | 424/101 X |
| 4,053,590 | 10/1977 | Bonsen et al. | 260/112 B X |
| 4,061,736 | 12/1977 | Morris et al. | 260/112 B X |
| 4,064,118 | 12/1977 | Wong | 260/112.5 R |
| 4,136,093 | 1/1979 | Bonhard et al. | 260/112.5 R |
| 4,320,111 | 3/1982 | Hirsch et al. | 260/112 B X |
| 4,401,652 | 8/1983 | Simmonds et al. | 260/112 B X |
| 4,473,496 | 9/1984 | Scannon | 260/112 B |
| 4,529,719 | 7/1985 | Tye | 260/112 B X |

OTHER PUBLICATIONS

Biochemistry, 11, No. 19, 3576–3582 (1972), Benesch et al.
Biochemical & Biophysical Res. Communic. 63, No. 4 (1975), 1123–1130, Benesch et al.
Fed. Proc. 34, No. 6, (1975), 1458–1460, Mok et al.
J. Biol. Chem., 254, No. 3 (1979), 702–707, McDonald et al.
J. Biol. Chem., 258, No. 19, (1983), 11890–11895, Didonato et al.

Primary Examiner—Howard E. Schain
Attorney, Agent, or Firm—Sughrue, Mion, Zinn, Macpeak & Seas

[57] ABSTRACT

Stroma-free hemoglobin cross-linked with reagents that mimic 2,3 diphosphoglycerate and transform stroma-free hemoglobin into a physiologically competent oxygen carrier which is retained in vivo for adequate periods of time and thus can be used in fluids for transporting oxygen; reagents for cross-linking stroma-free hemoglobin and method for cross-linking stroma-free hemoglobin.

42 Claims, No Drawings

INTRAMOLECULARLY CROSS-LINKED HEMOGLOBIN AND METHOD OF PREPARATION

The development of the present invention was supported by the University of Maryland and NIH(HL-13164).

FIELD OF THE INVENTION

The present invention relates to hemoglobin which has been intramolecularly cross-linked with reagents which transform hemoglobin into a physiologically competent oxygen carrier. As defined herein, "physiologically competent" or "physiologically acceptable" with respect to the oxygen carrier means that the oxygen carrier can absorb oxygen at the partial pressures of oxygen prevailing at the site of oxygenation of hemoglobin, e.g., in the lungs of men or other air-breathing organisms and in the gills of fish, and release it to the tissues of the same organisms in amounts which are life supporting at least when the organisms are in a resting state.

BACKGROUND OF THE INVENTION

1. Stroma-Free Hemoglobin

Intravenously injected (infused) crude hemolysates and extensive hemolytic processes produced in vivo by immunological reactions involving intravascular lysis of red blood cells, are known to produce a clinical syndrome characterized by disseminate intravascular coagulation. This syndrome is often fatal and is produced by the residual red blood cell walls (stroma) and their fragments, so infused into circulating blood. Stroma-free hemolysates do not show this toxicity (See Rabiner, S. F. et al, *J. Exp. Med.*, 126:1127 (1967)). As a result, it has been desired to use stroma-free hemoglobin as an oxygen carrier in cell-free transfusional fluids.

However, the use of stroma-free hemoglobin has the following two disadvantages. In vivo, the retention time of the stroma-free human hemoglobin is very short, i.e., it has a half-life on the order of 1–4 hours (See Rabiner, S. F., supra, and De Venuto, F. et al, *Transfusion*, 17:555 (1977)). "Half-life" is defined as the time necessary to eliminate 50% of the infused hemoglobin from circulating blood. Further, outside of the red blood cells, hemoglobin has a high affinity for oxygen which, in vivo, would prevent the release, i.e., the transport, of oxygen from hemoglobin to the tissues. These disadvantages are directly the result of the molecular structure of hemoglobin.

Hemoglobin is a tetrameric molecule having a molecular weight of 64,500 Daltons. The tetrameric molecule is formed of two pairs of alpha and beta subunits. The subunits are held together as a result of ionic and Van der Waals forces, and not as a result of covalent bonds. When hemoglobin is oxygenated, i.e., combined with oxygen, it readily forms alpha-beta dimers having a molecular weight of 32,250 Daltons. These dimers are not retained in vivo by the kidneys and are eliminated through the urine.

The tetrameric structure of hemoglobin also provides a binding site for 2,3-diphosphoglycerate. Inside red blood cells, 2,3-diphosphoglycerate combines with hemoglobin in order to decrease its oxygen affinity to a level compatible with oxygen transport. The binding of 2,3-diphosphoglycerate and hemoglobin is purely electrostatic and no stable covalent bonds are formed. Thus, when red blood cells are ruptured and 2,3-diphosphoglycerate is not retained inside the cells by the cell wall, it is released from hemoglobin. As a result, hemoglobin acquires a higher oxygen affinity. This prevents the transport of oxygen from hemoglobin to the tissues. The level of this higher affinity is sufficient such that the oxygen affinity can be considered "non-physiological".

Because of the many appealing qualities of hemoglobin i.e., its ability to reversibly bind oxygen, the low viscosity of a hemoglobin solution and its easy preparation and storage for long periods of time, various attempts have been made in order to overcome the above-described disadvantageous characteristics of stroma-free hemoglobin. These various attempts are discussed in more detail below.

2. Chemical Treatments for Preventing the Formation of Dimers

The formation of alpha-beta dimers, which are not retained in vivo, can be prevented by coupling the tetrameric molecules of hemoglobin with large molecular weight matrices, ranging from 20,000 to 275,000 Daltons, for example, matrices such as dextran (See Tam, S. C. et al, *Can. J. Biochem.*, 56:981 (1978) and Bonneaux, F. et al, *Experientia*, 37:884 (1981)) and hydroxyethyl starch (See Baldwin, J. E. et al, *Tetrahedron*, 37:1723 (1981)). This coupling prevents the elimination of hemoglobin in vivo from the kidneys by way of the urine. Other types of polymeric coupling employing collagen, collagen degradation products, and gelatin as a supporting matrix have also been employed (See U.S. Pat. No. 2,591,133, U.S. Pat. No. 3,057,782, and Bowes, F. et al, *Biochem. Biophys. Acta*, 168:341 (1968)). However, the oxygen affinity of the resulting coupled hemoglobin is even higher than that of stroma-free hemoglobin and thus hemoglobin coupled in this manner cannot be advantageously employed as an oxygen transport medium.

Other known treatments for preventing the formation of alpha-beta dimers are based on reactions which polymerize the tetrameric molecules of hemoglobin to form so-called "polyhemoglobins". Polyhemoglobins can be obtained using bifunctional reagents such as gluteraldehyde (See Hopwood, C. et al, *Histochem. J.*, 2:137 (1970) or diimidate esters (See Mock, W. et al, *Fed. Proc.*, 34:1458 (1975)) and U.S. Pat. No. 3,925,344). These bifunctional reagents form covalent bonds between the amino groups present on the surface of different hemoglobin molecules producing intermolecular cross-links. There are 40 or more of such amino groups belonging to lysyl residues on the surface of mammalian hemoglobins (44 in human hemoglobin) so that a large number of possible combinations of hemoglobin molecules occur. As a result, the polyhemoglobin reaction products are a heterogeneous mixture of various molecular species which differ in size and shape. The molecular weights thereof range from 64,500 to 600,000 Daltons. The separation of individual molecular species from the heterogeneous mixture is virtually impossible. In addition, although longer retention times in vivo are obtained using polyhemoglobins, the oxygen affinity thereof is higher than that of stroma-free hemoglobin.

Besides the various treatments discussed above which result in formation of heterogeneous mixtures of polyhemoglobin, reagents have been developed which are capable of producing an internal cross-link of the hemoglobin subunits with little or no formation of polyhemoglobins. More specifically, the formation of cross-links between the beta subunits of hemoglobin using 2-N-2-formyl-pyridoxal-5'-phosphate and borohydride has been carried out (See Bensch, R. et al, *Biochem. Biophys. Res. Comm.*, 62:1123 (1975)). The oxygen affinity of the thus treated hemoglobin is decreased to levels similar to that of normal blood. However, the reagent employed therein is very difficult and costly to synthesize, and thus the method is disadvantageous.

Other reagents have been employed in order to effect internal cross-linking of the hemoglobin subunits. These reagents are commonly known as "diaspirins". Diaspirins are diesters of bis-3,5-dibromosalicylate containing succinyl, fumaryl or other dicarboxylic acid residues. These reagents produce covalent cross-links between two beta or two alpha subunits of an individual hemoglobin molecule. While better results are obtained using liganded (oxy- or carboxy-) hemoglobin, such a treatment does not sufficiently affect the oxygen affinity characteristics of stroma-free hemoglobin and thus cannot be advantageously employed. (See Walder, J. A. et al, *J. Mol. Biol.*, 141:195 (1980), U.S. Pat. No. 4,061,736, U.S. Pat. No. 4,001,200, U.S. Pat. No. 4,001,401, and U.S. Pat. No. 4,053,590)).

In U.S. Pat. No. 4,473,496, linear alpha-omega or heterocyclic polyaldehydes containing negatively charged groups are described as suitable for both decreasing the oxygen affinity of hemoglobin and for producing inter- and intramolecular cross-linking of hemoglobin. These reagents include carbohydrate-containing molecules such as mono- and polyphosphorylated nucleotides partially oxidized with periodate, so as to obtain aldehydic groups. The coupling reaction is based on the formation of Shiff bases of the aldehydic groups with the amino groups of the hemoglobin molecule. The Shiff bases are then transformed into covalent bonds by reduction with sodium or potassium borohydride, or another strong reducing agent.

The above-described treatments, i.e., those based on the use of aldehydic reagents, have a further disadvantage in that they must be performed in the absence of air and oxygen, i.e., they must be performed on deoxyhemoglobin. That is, in the presence of air and oxygen, the reaction does not occur or does not produce the desired effects on the characteristics of hemoglobin. Also, oxygen-absorbing chemicals, e.g., sodium dithionite, cannot be used because they interfere with the reagents used for the treatment. Thus, these treatments must be disadvantageously performed in a closed environment and oxygen is removed either by flushing and/or bubbling the solution with nitrogen or some other inert gas, or using mechanical evacuation, or combining the two procedures. These treatments always produce disadvantageous denaturation of 2 to 5% of the hemoglobin present, i.e., denatured hemoglobin irreversibly loses its ability to combine with and transport oxygen.

3. Chemical Treatments for Decreasing the Oxygen Affinity of Stroma-Free Hemoglobin The most widely used chemical modification of stroma-free hemoglobin so as to decrease the oxygen affinity thereof employs the use of pyridoxal-5'-phosphate and sodium or potassium borohydride (see Bensch, R. et al, *Biochem.*, 11:3576 (1972)). The resulting product is commonly referred to as "PLP-hemoglobin" and has satisfactory oxygen affinity, i.e., oxygen affinity very near that of the red cells present in normal blood. However, in order to be effective, this treatment must be performed on deoxy-hemoglobin i.e., hemoglobin devoid of oxygen. Thus, this procedure must disadvantageously be carried out in a closed environment in the absence of air and oxygen as described above for reactions involving aldehydic groups.

Other known chemical modifications of hemoglobin have been carried out using phosphoric acid derivatives of carbohydrates (e.g. glucose-6-phosphate) (See McDonald, M. J. et al, *J. Biol. Chem.*, 254:702 (1979)); carbamylation (See Manning, J. S. *Meth. Enz.*, 76:159 (1981) and carboxymethylation (See DiDonato, A. et al, *J. Biol. Chem.*, 258:11890 (1983)). In each of these treatments, the amino-terminal end of the beta subunit of hemoglobin is permanently substituted with the above-described reagents.

In addition, none of these chemical treatments discussed in this part stabilize the tetrameric structure of hemoglobin so as to prevent the formation of alpha-beta dimers. Thus, the resulting hemoglobins do not have prolonged retention times in vivo.

4. Combined Chemical Treatments for Preventing the Formation of Alpha-Beta Dimers and Decreasing the Oxygen Affinity of Stroma-Free Hemoglobin As discussed above, the production of physiologically competent stroma-free hemoglobin-based oxygen carriers necessitates two separate treatments. That is, one treatment is necessary for preventing the formation of alpha-beta dimers in vivo and a second treatment is required for decreasing its oxygen affinity. The most widely employed combination of treatments is that of reacting gluteraldehyde with PLP-hemoglobin to form pyridoxylated polyhemoglobins (See Seghal, L. K. et al, *J. Surg. Res.*, 30:14 (1981)). Intramolecular cross-linking of PLP-hemoglobin has also been obtained using diaspirins (See, Tye, R. et al, *Prog. Clin. Biol. Res.*, 22:41 (1983)).

Again, the above-described chemical treatments must be disadvantageously performed on deoxyhemoglobin in the absence of oxygen or air in closed containers under, for example, nitrogen or some other inert gas with or without mechanical evacuation without the aid of oxygen-absorbing chemicals. Otherwise, hemoglobin with very high oxygen affinity is obtained, i.e., higher than that of stroma-free hemoglobin.

It should be noted that only stroma-free hemolysates or washed red blood cells are utilized in the above-cited articles. That is, purification procedures for isolating the hemoglobin component of the stroma-free hemolysates are not described therein. Thus, what is defined as stroma-free hemoglobins therein is in actuality stroma-free hemolysates.

More specifically, about 95% of the hemolysate components is hemoglobin. The remainder consists of proteins and polypeptides whose pharmacological and immunological toxicity is not known. When used for infusion in animals, several grams of hemolysate-containing hemoglobin are injected. Thus, undesirably, hundreds of milligrams of substances of unknown biological activity are also infused into animals when employing a hemolysate.

It should also be noted that in the above-cited references, purification procedures for isolating the desired hemoglobin products from the reaction mixture are not described therein. It is impossible to avoid the presence of overreacted and underreacted hemoglobins in the reaction mixtures. These products do not have the desired functional and molecular characteristics.

For the above reasons, it is advantageous to perform chemical treatments on purified hemoglobins, and then to purify the product of the reaction.

SUMMARY OF THE INVENTION

Accordingly, an object of the present invention is to provide a cross-linked stroma-free hemoglobin having a physiologically acceptable oxygen affinity.

Another object of the present invention is to provide a cross-linked stroma-free hemoglobin which substantially does not form alpha-beta dimers in vivo.

Still another object of the present invention is to provide a cross-linked stroma-free hemoglobin which has a half-life in vivo of at least 6 hours.

A further object of the present invention is to provide a cross-linked stroma-free hemoglobin having a low viscosity so as to facilitate fluid circulation.

A still further object of the present invention is to provide a cross-linked stroma-free hemoglobin which is chemically stable for at least one year.

An additional object of the present invention is to provide a cross-linked stroma-free hemoglobin whose production can be easily carried out and which can be easily stored and in a stable manner.

Another object of the present invention is to provide a cross-linked stroma-free hemoglobin which is devoid of chemical or biological toxicity.

Still another object of the present invention is to provide a reagent for cross-linking hemoglobin so as to simultaneously provide a physiologically acceptable oxygen affinity thereof and prevent the formation of alpha-beta dimers in vivo.

Also, another object of the present invention is to provide a method for cross-linking stroma-free hemoglobin using a reagent which simultaneously provides a physiologically acceptable oxygen affinity thereof and prevents the formation of alpha-beta dimers in vivo.

A still further object of the present invention is to provide a method of cross-linking a stroma-free hemoglobin which can be conducted in a single step in the presence of air and oxygen so as to obtain compounds with the desired oxygen affinity.

The above objects of the present invention have been met by at least one cross-linking reagent selected from the group consisting of compounds of general formulae (I) and (II):

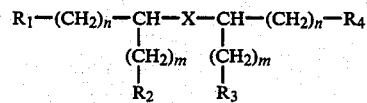     (I)

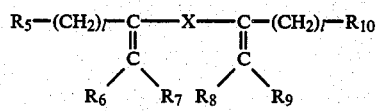     (II)

wherein one of $R_1$ or $R_2$ represents an electron-withdrawing atom or group, and the other of $R_1$ or $R_2$ represents a leaving atom or group or an electron-withdrawing group containing a leaving atom or group; one of $R_3$ or $R_4$ represents an electron-withdrawing atom or group, and the other of $R_3$ or $R_4$ represents a leaving atom or group or an electron-withdrawing group containing a leaving atom or group; $R_5$ and $R_{10}$, which may be the same or different, each represents an electron-withdrawing atom or group or an electron-withdrawing group containing a leaving atom or group; one of $R_6$ or $R_7$ represents a hydrogen atom, an alkyl group, an aryl group, or a heterocyclic group, and the other of $R_6$ or $R_7$ represents a leaving atom or group; one of $R_8$ or $R_9$ represents a hydrogen atom, an alkyl group, an aryl group or a heterocyclic group, and the other of $R_8$ or $R_9$ represents a leaving atom or group; X represents a linking atom or group, $n=0$ to 4, $m=0$ to 4 and $l=0$ to 4.

In another embodiment of this invention, the invention provides stroma-free hemoglobin cross-linked with at least one cross-linking reagent selected from the group consisting of compounds of general formulae (I) and (II) above.

In still another embodiment of this invention, the invention provides a method of cross-linking stroma-free hemoglobin with at least one cross-linking reagent selected from the group consisting of compounds of general formulae (I) and (II) above.

DETAILED DESCRIPTION OF THE INVENTION

As discussed above, the present invention provides stroma-free hemoglobin which has been cross-linked with at least one cross-linking reagent selected from the group consisting of compounds of the general formulae (I) and (II):

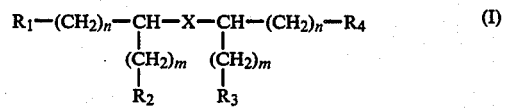     (I)

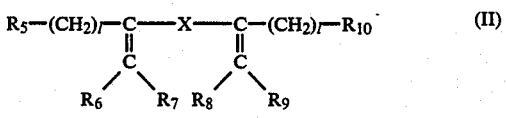     (II)

wherein one of $R_1$ or $R_2$ represents an electron-withdrawing atom or group, and the other of $R_1$ or $R_2$ represents a leaving atom or group or an electron-withdrawing group containing a leaving atom or group; one of $R_3$ or $R_4$ represents an electron-withdrawing atom or group, and the other of $R_3$ or $R_4$ represents a leaving atom or group or an electron-withdrawing group containing a leaving atom or group; $R_5$ and $R_{10}$, which may be the same or different, each represents an electron-withdrawing atom or group or an electron-withdrawing group containing a leaving atom or group; one of $R_6$ or $R_7$ represents a hydrogen atom, an alkyl group, an aryl group, or a heterocyclic group, and the other of $R_6$ or $R_7$ represents a leaving atom or group; one of $R_8$ or $R_9$ represents a hydrogen atom, an alkyl group, an aryl group or a heterocyclic group, and the other of $R_8$ or $R_9$ represents a leaving atom or group; X represents a linking atom or group, $n=0$ to 4, $m=0$ to 4 and $l=0$ to 4.

An "electron-withdrawing atom or group" is well known in the art and is an electrophilic species which pulls electrons away from bonds towards itself by either resonance or by inductive effects.

The electron-withdrawing atom or group represented $R_1$, $R_2$, $R_3$, $R_4$, $R_5$ and $R_{10}$ can include, among other species, a member selected from the group consisting of CN, $NO_2$, halogen (e.g., Cl, Br, F, etc.), $S(O)R_{11}$, $S(O_2)R_{11}$, halogen (e.g., Cl, Br, F, etc.), $S(O)R_{11}$, $S(O_2)R_{11}$, $C(O)R_{11}$, wherein $R_{11}$ is selected from the group consisting of a hydrogen atom, a $C_1$-$C_{12}$ alkyl group which may be substituted or unsubstituted, a substituted or unsubstituted mono or bicyclic aryl group or a substituted or unsubstituted heterocyclic group. Examples of the substituents on the alkyl, aryl or heterocyclic groups include halogen, CN, $C_1$-$C_{12}$ alkyl, phenyl which may be substituted, $NO_2$, OH, or $C_1$-$C_{12}$ alkoxy.

Examples of electron-withdrawing groups containing a leaving atom or group can include, among other groups, a member selected from the group consisting of $R_{12}P(O)OR_{12}$, $PO(OR_{12})_2$, $OP(O)(OR_{12})_2$ and $CO_2R_{12}$, wherein $R_{12}$ is defined as above for $R_{11}$ and the moiety $OR_{12}$ leaves as the leaving group, and additionally can be a halogen atom and $P(O)(R_{13})_2$, $S(O)R_{13}$, $S(O_2)R_{13}$ and $C(O)R_{13}$, wherein $R_{13}$ is a halogen atom.

Examples of suitable heterocyclic groups include 5- or 6-membered heterocyclic rings such as imidazolyl and pyrazinyl, both of which may be substituted or unsubstituted with, for example, CN, $NO_2$, OH, halogen, $C_1$-$C_{12}$ alkyl, $C_1$-$C_{12}$ alkoxy, or phenyl which may be substituted. Further, the heterocyclic group can contain oxygen or sulfur in place of nitrogen.

$R_1$, $R_2$, $R_3$, $R_4$, $R_5$ and $R_{10}$ as electron-withdrawing atoms or groups are preferably CN and $SO_2R_{11}$.

$R_1$, $R_2$, $R_3$, $R_4$, $R_5$ and $R_{10}$ as electron-withdrawing groups containing a leaving group are preferably $CO_2R_{12}$, $PO(OR_{12})_2$ where $R_{12}$ is as above defined, and $SO_2R_{13}$ where $R_{13}$ is as above defined, for example, $CO_2C_2H_5$, $CO_2C_6H_4(NO_2)$, $P(O)(Cl)_2$, $SO_2Cl$, etc.

A "leaving atom or group" is well known in the art and is an electron-rich species which can be an atom or a group of atoms which, by virtue of its capability to stabilize itself by delocalization of its excess negative charge through either resonance effects, inductive effects, or charge dissipation, can easily leave, thus making room for an incoming nucleophile. In some instances, the leaving atom or group may act as an electron withdrawing group.

The leaving atom or group represented by $R_1$, $R_2$, $R_3$, $R_4$, $R_6$, $R_7$, $R_8$ and $R_9$ can include, among other groups, a halogen atom and $OR_{11}$, wherein $R_{11}$ is as described above, preferably $CH_3$, $C_2H_5$, $C_6H_5$ or $CH_2C_6H_5$.

Examples of groups other than a leaving atom or group for $R_6$, $R_7$, $R_8$ and $R_9$ include a hydrogen atom, a $C_1$-$C_{12}$ alkyl group, an aryl group, or a heterocyclic group, which may be substituted or unsubstituted as described above for $R_1$; preferably $CH_3$, $C_2H_5$, a phenyl group, or an imidazolyl group.

As defined, herein, a "linking atom or group" is an electrophilic species serving as an "electron-sink" for the two connecting functional groups which are the potential electron-acceptors.

The linking atom or group represented by X can include, among other groups, $SO_2$, SO, $P(O)(OR_{11})$, CO, Se, Te and Sr, wherein $R_{11}$ is as defined above. X is preferably $SO_2$, SO, $P(O)(OR_{11})$ or CO.

In the present invention, m=0 to 4, preferably 0 to 2; n=0 to 4, preferably 0 to 2; and l=0 to 4, preferably 0 to 2.

In formula (I), as to $R_1$, $R_2$, $R_3$ and $R_4$ bonded directly or indirectly to X, one of $R_1$ or $R_2$ and one of $R_3$ or $R_4$ must be a leaving atom or group or must be an electron withdrawing group containing a leaving atom or group, such as a halogen atom or $OR_{11}$, wherein $R_{11}$ is as defined above.

Specific examples of the cross-linking agents of general formulae (I) or (II) of the present invention include:

Ethyl 2,2' sulfonyl-bis-cyanoacetate (hereinafter "ESBCA") which is represented by the formula set forth below:

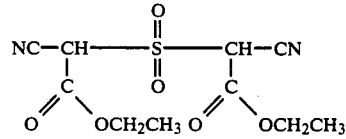

Diethyl 2,2'-sulfonyl-bis-malonate (hereinafter "DSBM") which is represented by the formula set forth below:

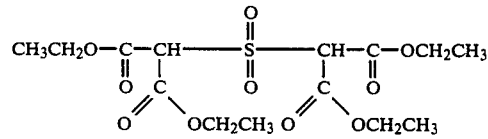

Ethyl 2,2'-sulfonyl-2,2'-benzenesulfonyl-bis-acetate (hereinafter "ESBSBA") which is represented by the formula set forth below:

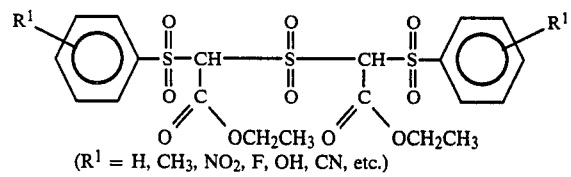

($R^1$ = H, $CH_3$, $NO_2$, F, OH, CN, etc.)

2,2'-Sulfonyl-2,2'-imidazole-N-sulfonyl-bis-acetonitrile (hereinafter "SISBA") which is represented by the formula set forth below:

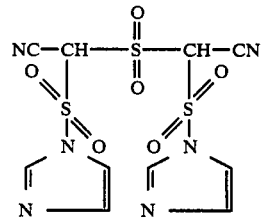

Methyl 2,2'-sulfonyl-bis-cyanoacetate (hereinafter "MSBCA") which is represented by the formula set forth below:

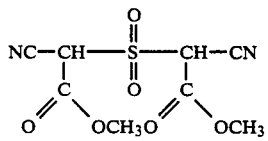

2,2'-Methoxymethylene-2,2'-sulfonyl-bis-acetonitrile (hereinafter "MMSBA") which is represented by the formula set forth below:

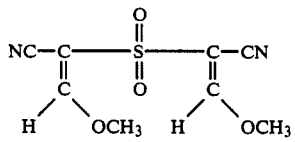

Dimethyl 2,2'-methoxyphosphinyldiene-2,2'-methoxymethylene-bis-methanephosphonate (hereinafter "DMMBMP") which is represented by the formula set forth below:

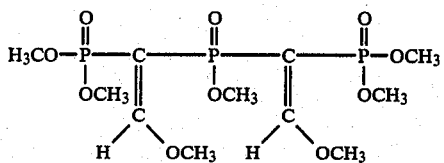

SYNTHESIS OF REAGENTS OF THE PRESENT INVENTION

The reagents of the present invention, wherein X is $SO_2$, can be prepared by the following methods. These syntheses would also be analogous where X is other than $SO_2$. All of the syntheses can begin with the following known Compounds A and B.

COMPOUND A (2,2'-sulfonyl-bis-acetonitrile)

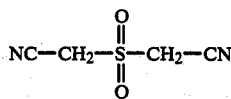

and
COMPOUND B (2,2'-sulfonyl-bis-acetate)

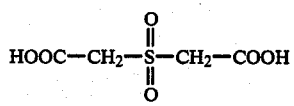

Known compounds A and B can be obtained by reacting either chloroacetonitrile or chloroacetic acid with sodium sulfide nonahydrate, and oxidizing the resulting thiodiacetonitrile or thiodiacetic acid with hydrogen peroxide in the presence of acetic acid and sulfuric acid. (See McCormick, J. E. et al, *J. Chem. Soc. Perkin I*, 1335 (1972); Baliah, V. et al, *J. Chem. Soc.* 3068 (1954); and Alden, J. P. et al, *J. Amer. Chem. Soc.*, 56:413 (1934)).

The synthesis of ESBCA can be accomplished by treatment of Compound A with ethylchloroformate in the presence of sodium hydride, according to the scheme:

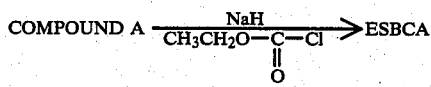

DSBM can be obtained in an analogous manner as described for ESBCA only beginning from the diethyl ester of Compound B, which is obtained by esterification of Compound B with ethanolic hydrogen chloride.

ESBSBA can be obtained, beginning with the diethyl ester of Compound B, by reaction with the appropriately substituted benzene sulfonylchloride in the presence of sodium hydride according to the scheme:

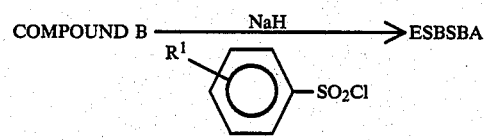

SISBA can be obtained, beginning with Compound A, by reacting with 1,1'-sulfonyl-bis-imidazole (See Staab, H. A. et al, *Ann. Chem.*, 694:86 (1966)) in the presence of sodium hydride according to the scheme:

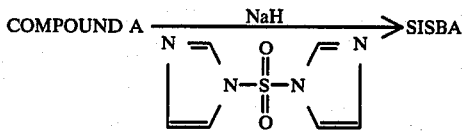

MSBCA can be synthesized in an analogous manner described above for ESBCA by substituting methyl chloroformate for ethyl chloroformate.

MMSBA can be synthesized by treating Compound A with trimethyl orthoformate in the presence of catalytic amounts of sulfuric acid.

DMMBMP can be obtained commencing from dimethyl 2,2'-methoxyphosphinylidene-bis-methanephosphonate [((OCH$_3$)$_2$P(O)CH$_2$)$_2$-P(O)(OCH$_3$)] (hereinafter "DMBMP"), prepared according to the procedure described for the corresponding ethyl analogue (See Gilmore, W. F., et al, *ACS Symp. Ser.*, 171:611-14 (1981)). The latter compound is treated with trimethyl orthoformate, catalyzed by trifluoroacetic acid to yield DMMBMP, according to the scheme:

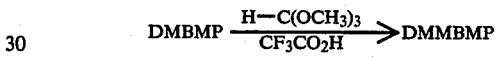

GENERAL METHOD FOR THE SYNTHESIS OF THE REAGENTS, MSBCA, ESBCA, DSBM, ESBSBA, AND SISBA

The above-identified reagents can be prepared by employing either Coupound A (MSBCA, ESBCA and SISBA) or the diethyl ester of Compound B (DSBM and ESBSBA) as the starting materials, as discussed in more detail below.

In a 150 ml dry three-neck flask fitted with an $N_2$-inlet, an addition funnel, a serum cap and a reflux condenser, a slurry of sodium hydride is added (the slurry is pre-washed three times with dry toluene to remove the adhering oil) (6 milliequivalents) in dry diethyl ether ("ether") or in dry tetrahydrofuran (THF) (30 ml). A solution of either Compound A or the diethyl ester of Compound B (3 milliequivalents) in dry ether or dry THF (30 ml) is slowly added drop-by-drop through the addition funnel while stirring the mixture on a magnetic stirrer and cooling, if necessary. The mixture is stirred at room temperature while maintaining the N-atmosphere for an additional 2-3 hour period. Then a cold solution of 6 milliequivalents of either methyl chloroformate (in the synthesis of MSBCA) or ethyl chloroformate (in the synthesis of ESBCA or DSBM) or substituted benzene sulfonyl chloride (in the synthesis of ESBSBA) or 1,1'-sulfonyl-bis-imidazole (in the synthesis of SISBA) is injected through the serum cap with a hypodermic syringe needle. The reaction mixture is stirred at room temperature overnight and the precipitate formed is filtered off. The filtrate is evaporated to dryness on a rotary evaporator using a water-bath whose temperature does not exceed 40° C. To the residue, approximately 50 ml of dry ether or dry THF is added, and any precipitate which separates at this point is filtered off. The filtrate once again is evaporated to dryness, this time after drying over anhydrous sodium sulfate for several hours. The solid products obtained can be recrystallized from appropriate solvents such as ethyl acetate, acetonitrile, toluene, ethanol, methanol or a combination of solvents such as ethyl acetate and petroleum ether, toluene and hexane, etc.

The following example is given to illustrate more specifically the synthesis of compounds of the general formulae (I) and (II). Unless otherwise indicated herein, all parts, percents, ratios and the like are by weight.

SYNTHESIS EXAMPLES

A. Synthesis of MMSBA

A mixture of 2,2'-sulfonyl-bis-acetonitrile (0.5 g, 3.47 mmol), dry acetonitrile (15 ml), trimethyl orthoformate (15 ml, 137 mmol) and concentrated sulfuric acid (4 drops) was heated at reflux under nitrogen gas for 15 hours. The reaction mixture was cooled and evaporated to dryness on a rotary evaporator using a water bath maintained at 50° C. The solid product obtained was triturated with 10 ml of ethyl acetate and filtered. The precipitate was recrystallized from xylene into colorless flakes (0.58 g, 2.54 mmol, 73% yield); mp 204°–205° C., $^1$HNMR (DMSO-$d_6$) δ 4.23 (s, 6H, 2OCH$_3$), 8.37 (s, 2H, 2=CH); IR (KBr) 3030 (=CH), 2250 (CN), 1590 (C=C), 1300, 1170 (SO$_2$) cm$^{-1}$; UV(MeOH) $\lambda_{max}$ 248 nm. The elemental analysis (%) calculated for C$_8$H$_8$N$_2$SO$_4$ (228.2) was as follows: C, 42.10; H, 3.53; N, 12.28. The elemental analysis (%) found was as follows: C, 42.43; H, 3.67; N, 12.05.

B. Synthesis of DMMBMP

A mixture of dimethyl 2,2'-methoxyphosphinylidene-bis-methanephosphonate (0.65 g, 2 mmol), dry toluene (25 ml), trimethyl orthoformate (16 ml, 146 mmol) and trifluoroacetic acid (5 drops) was heated at reflux under N$_2$ for 12 hrs. The reaction mixture was cooled and evaporated to dryness on a water-bath maintained at 60° C. The solid residue obtained was recrystallized from xylene to obtain DMMBMP.

The term "hemoglobin" as used in the present invention and appended claims means hemoglobin of human, mammal, or any other animal species origin, synthetically produced hemoglobins, hemoglobins obtained in vitro from eukaryotic or prokaryotic cell lines which have been cloned to produce hemoglobin or its subunits or hemoglobins obtained in mutant form, chemically modified form, or combined form, i.e., a combination of subunits from different species. Examples of hemoglobins include human, marine mammalian, equine, porcine, ovine, bovine, and simian hemoglobin and additionally fish hemoglobin. Bovine hemoglobin is preferred and can be obtained, for example, from blood collected from the jugular vein of a cow under sterile conditions into glass bottles containing an acid-citrate-dextrose (ACD) solution (i.e., containing an anticoagulant) (Fenwal Inc.)) to a final 1:8 v/v. The only requirement is that the hemoglobin employed exhibit high affinity for polyanions, e.g., 2,3-diphosphoglycerate, other polyphosphates, nucleotides and polynucleotides, or other negatively charged mono- or polyvalent anions which regulate hemoglobin's oxygen affinity properties.

The hemoglobin to be treated in the present invention is stroma-free, i.e., substantially free of either cell walls or degradation products of the cell walls, or other phospholipids. Stroma-free red cell hemolysates can be used if desired, although purified hemoglobin is preferred.

The reactivity of hemoglobin with polyanions provides the means by which reagents of the present invention can be reacted with specific sites on the hemoglobin molecule. In the present invention, polyvalent reagents have been designed to bring, by virtue of their anionic characteristics, amide or enamine bond-forming groups near selected amino groups in the hemoglobin molecule so as to form intramolecular covalent cross-links of the hemoglobin subunits. Although the cross-linking is essentially intramolecular, intermolecular cross-links may also be produced and utilized.

The cross-linking bridges inserted into the hemoglobin molecule have the electronegativity characteristics necessary for simulating the presence of 2,3-diphosphoglycerate, thereby adjusting the oxygen affinity of stroma-free hemoglobin to physiologically acceptable levels.

The reagents of the present invention produce viable products by reacting both with liganded (oxy-, carboxy-, or derivatives thereof) and unliganded (deoxy-) hemoglobin. In additaon, ferric hemoglobin and its derivatives can also be utilized in the present invention. When the reagent of the present invention is reacted with deoxyhemoglobin, the reaction can be performed in the presence of oxygen-absorbing chemicals, for example, sodium dithionite, without deleterious effects.

In the present invention, only a single chemical treatment is necessary for both adjusting the oxygen affinity and stabilizing the tetrameric structure of hemoglobin. Also, it is not necessary to stabilize newly introduced chemical bonds using borohydride salts in order to form covalent bonds as occurs with the known reactions involving aldehydes and polyaldehydes discussed above.

Since the reagents of the present invention are highly specific for selected groups on the hemoglobin molecule, reaction products within limited heterogenity are obtained. Thus, a high yield of the desired modification product is also obtained. The specificity and necessity of only a single chemical treatment in the present invention simplifies the purification procedures as to the product obtained so that a high yield of essentially uniform molecular species is possible.

The cross-linking of hemoglobin as in the present invention prolongs the retention time of the hemoglobin after transfusion in animals. (See Tye, R. et al, *Prog. Clin. Biol. Res.*, 122:41 (1983) and Greenburgh, H. G. et al, *Prog. Clin. Biol. Res.*, 122:9 (1983)). The presence of the cross-links also stabilizes the hemoglobins with respect to physical and chemical agents so as to allow stable and prolonged storage at low cost. Further, the cross-linked hemoglobin of the present invention is very soluble in water and all of the hemes participate in binding and transporting oxygen. Moreover, the viscosity of a 7% w/v solution of hemoglobin, i.e., a solution of hemoglobin normally used for infusion in animals, at 37° C. is less than that of normal blood, and thus such a solution can be advantageously employed.

The cross-linked hemoglobin of the present invention can be infused after solution in standard renal dialysis fluid (e.g., Erilyte 8306, Erika, Inc.) at a concentration of 7% w/v, after filtration through a 0.22 micron filter or some other procedure so as to ensure sterility of the fluids. In mammals, generally 10 to 100% of the circulating blood can be replaced with the cross-linked hemoglobin of the present invention.

Fluids containing oxygen carriers can also be used to prime the pumps necessary to drive surgical equipment like that which provides extracorporeal blood circulation. This will save the several liters of blood at present used for this purpose. These fluids can be employed in emergency situations for shock therapy and also have utility in veterinary uses where in the past sources of transfusional fluids have been scarce.

In addition, the oxygen carrier is completely soluble in water and can be used in fluids alone or with other oxygen carrier fluids and plasma expanders for transporting oxygen, for example, to isolated perfused organs, to oxygen-consuming environments, or to vial tissues in vivo as components of transfusional agents for medical and veterinary, clinical and surgical practice.

Also, the risks of transmission of infectious diseases (e.g., hepatitis, AIDS, etc.), which can occur with blood tranfusions, will be absent using oxygen-carrier fluids containing the cross-linked hemoglobin of the present invention.

A. Preparation of Stroma-Free Hemoglobin

Stroma-free hemoglobin can be prepared, for example, from erythrocytes separated either from freshly drawn blood, from outdated blood, or from pelleted erythrocytes. In order to collect the erythrocytes, the blood samples are washed several times with an isotonic solution, e.g., 5 mM phosphate buffer, 150 mM NaCl, pH 7.5 and the plasma is removed by centrifugation at 3,000 rpm. The washed erythrocytes are then hemolyzed with an equal volume of a hypertonic solution, e.g., 5 mM phosphate buffer, pH 7.5. The cellular debris (stroma) still present in the hemolysate is then removed by subsequent filtration through a 0.5 and a 0.2 micrometer Pellicon cassette (Millipore) or equivalent devices. The filtered hemolysate is referred to as a "stroma-free" hemolysate since it is devoid of particles having diameters larger than 0.2 micrometer. Using a Millipore Pellicon cassette with a nominal 10,000 MW cutoff, the obtained hemolysate is concentrated and equilibrated with desired buffer, e.g., MES, acetate, MOPS, Bis-Tris, Tris or Hepes, preferably 20 mM Tris buffer, pH 8.0.

The hemoglobin is purified from non-hemoproteins, from non-hemoglobinic-hemoproteins and from organic and inorganic contaminants by absorption and subsequent elution on anionic or cationic resins. Examples of suitable anionic resins include DEAE 5PW (Walters) and QAE-25/50 (Pharmacia). Examples of suitable cationic resins include 8PC 25/50 (Pharmacia) and SP 5PW (Waters). In the present invention, anionic resins are preferred since they completely remove the organic phosphates that can be bound to the hemoglobin.

Removal of organic phosphates, e.g., 2,3-diphosphoglycerate, is necessary in human hemolysates because the site of choice of the cross-linking reaction is the same as that occupied by 2,3-diphosphoglycerate in hemoglobin.

The above-described procedures are generally carried out at a temperature of 4° C. to 10° C. After equilibration with the desired buffer, the purified, stroma-free hemoglobin can be cross-linked, as described in more detail below.

B. Cross-linking of Stroma-Free Hemoglobin

The cross-linking in the present invention refers to intra-molecular cross-links which result in undissociable tetrameric hemoglobin molecules. The cross-linking reagents of the present invention have been designed to carry negative charges so as to mimic the function of the negatively charged 2,3-diphosphoglycerate, i.e., to lower the oxygen affinity of hemoglobin so as to have an efficient oxygen release in vivo at the tissue level for the host of interest. In addition, the reagents of the present invention form stable covalent bonds with the amino groups present at the site where hemoglobin binds 2,3-diphosphoglycerate. Other sites of reaction are possible, and acceptable in producing the stabilization of the hemoglobin molecules necessary for physiological oxygen transport. When the reaction with the amino group occurs outside of the 2,3-diphosphoglycerate binding site, intermolecular cross-links can be produced. When the reaction occurs inside the 2,3-diphosphoglycerate binding site, which is by far the major reaction, alpha-alpha and/or beta-beta hemoglobin subunit links are formed, which prevent the dissociation of the hemoglobin molecule into the alpha-beta dimers which, as discussed above, are rapidly eliminated with urine after infusion.

The cross-linking can be performed when hemoglobin either is liganded or unliganded. In order to cross-link the liganded form, the reagent is added to the purified stroma-free hemoglobin kept under a stream of the necessary gaseous ligands, e.g., oxygen or carbon monoxide, with continuous stirring, at between 4° C. and 10° C. In order to cross-link the unliganded form, the reagent of the present invention is added to the hemoglobin which is kept in a closed container under nitrogen or some other inert gas at atmospheric pressure. Residual oxygen is eliminated by the addition of oxygen-absorbing chemicals, for example, sodium dithionite in an amount of from 0.5 to 3 mg/ml.

The reaction of the present invention is performed using a molar equivalency or molar excess of the reagent to hemoglobin. Typically, the molar ratio of reagent to hemoglobin is 1:1 to 1:10, preferably 1:2 to 1:6. In addition, typically, the hemoglobin concentration is 3% w/v to 9% w/v, preferably 6% w/v in 0.01M Bis-Tris buffer, pH 6.8. The reaction is allowed to proceed for a necessary amount of time at the desired temperature, generally for about 15 minutes to 3 hours and at 10° C. to 37° C.; preferably 25° C. to 30° C.

The reaction of the present invention is terminated by passing the reaction mixture through a molecular sieving column, e.g., Sephadex column, using pressure (about 1–2 p.s.i.) generated by the same gas employed during the reaction. This step eliminates the excess reagent used for cross-linking and can be used for equilibrating the hemoglobin with buffers appropriate for subsequent manipulations.

For the purpose of the present invention, it is preferred to obtain pure and homogeneous products. Thus, the cross-linked hemoglobin is further purified by chromatography on anionic or cationic resins in order to eliminate over- or under-reacted proteins resulting from the chemical reaction. Examples of such anionic and cationic resins include DEAE 5PW (Waters), SP 5PW (Waters), or QAE-H 25/50 SPC-25/50 (Sephadex). Gradients made by mixing 5 mM Tris and 5 mM Tris and 150 mM NaCl can be used for the elution. The purified cross-linked hemoglobin is collected and dialyzed three times with 1:20 v/v freshly prepared dionized water.

The cross-linked hemoglobin can be stored in water at −80° C. Storage at higher temperatures, between −80° and 4° C. can be carried out upon addition of dextran 70 (e.g. 6% w/v) in 0.9% w/v NaCl and/or reducing agents like ascorbic acid (e.g., 3 mg/ml) together with a chelating agent such as EDTA (e.g., 0.01–0.1 mg/ml) or vitamin E (e.g., 0.5 mg/ml). In this manner, the cross-linked hemoglobin is stable for weeks to, at the very least, several months.

C. Analyses for Purity and Homogeneity

The purity and homogeneity of the cross-linked hemoglobin can be assessed on microzone electrophoresis using cellulose acetate membranes (Beckman Instr. Publication No. 015-083630-C). The pure compound shows a single sharp band migrating towards a positive pole at a velocity higher than that of untreated hemoglobin.

The absence of intermolecular cross-links can be assessed by gel filtration (See Ackers, G., *Adv. Protein Chem.*, 24:343 (1972)) ultracentrifuge analysis (See Schachman, H. K., *Biochem.*, 2:884 (1963)) or other techniques which show the absence of polyhemoglobins.

The extent of intramolecular cross-linking can be assessed using SDS urea-gel electrophoresis. (See Swank, R. T., et al, *Anal. Biochem.*, 39:462 (1971)). In this method, the hemoglobin is unfolded with SDS and disulfide bridges are broken so that the velocity of electrophoretic migration inside the matrix of the supporting gel is determined only by the size, i.e., the molecular weight of its monomeric subunits. In the absence of the cross-linking modifications, hemoglobin in SDS electrophoresis produces one band corresponding to a molecular weight of 16,000 Daltons as is expected from the size of its monomeric subunits. On the other hand, if it is cross-linked, bands corresponding to polymeric units are obtained. Intramolecular cross-links produce the appearance of a 32,000 Dalton component corresponding to cross-linked subunit dimers. The non-cross-linked subunits continue to appear as a band of 16,000 Daltons. It will be easily recognized by one skilled in the art that the molecular weights given herein are as to human hemoglobin. For other species, these molecular weight values may differ somewhat but the principles involved are the same.

If the cross-linked dimer is between like subunits, the hemoglobin tetramer becomes undissociable at acid pH, and at neutral pH at high ionic strength, e.g., 1M NaCl, because the formation of dimers under these conditions is prevented.

The presence of dimer formation in the hemoglobin solution can be ascertained by measuring the sedimentation velocity of the hemoglobin. The sedimentation constants, $S_{20,w}$, for tetramers and dimers is 4.4 and 2.8, respectively (See Schachman, supra). Alternatively, dissociation of hemoglobin into dimers can be measured by gel filtration (See Ackers, supra).

The ability of hemoglobin to reversibly bind oxygen is dependent upon the ferrous state, i.e., oxidation state, of the iron of the heme. Thus, to maximize reversible oxygen binding capability, the process of the present invention and purification steps should be conducted under conditions that do not produce irreversible oxidation of the iron atom to its ferric form. Analyses of the absorption spectra of hemoglobin in the visible region can be employed in order to estimate the amount of ferric hemoglobin present in the final product (See Benesch, R. et al, *Anal. Biochem.*, 11:81 (1965)).

D. Determination of Oxygen Affinity

Oxygen affinity of cross-linked hemoglobin can be measured using the Hemoscan (trade name for an oxygen dissociation analyzer produced by Aminco) or the Gill cell (described in Dolman, D., et al, *Anal. Biochem.*, 87:127 (1978)).

These measurements are preferably performed at 37° C. at pH 7.4 in 0.15M Tris buffer and 0.15M NaCl, so as to mimic the physiological conditions in vivo. The oxygen absorption by hemoglobin is characterized by two parameters. One is the value of "$P\frac{1}{2}$," i.e., the partial pressure of oxygen sufficient for saturating 50% of the hemogloblin present in solution. The other is the value of "n" in the Hill equation (Wyman J., *Adv. Prot. Chem.*, 19:223 (1964)) which at best simulates the data and which is the expression of the oxygen binding cooperativity of the hemoglobin in solution. In vivo in humans, both parameters affect the amount of oxygen transported by hemoglobin from the lungs to the tissues. Inside the red cells, human hemoglobin has values of $P\frac{1}{2}=27$ mmHg and n near 3.0. Using the Hill equation and assuming that the partial pressure of oxygen in the lungs is 100 mmHg, and that at the tissue it is 30 mmHg (Bard, P., *Medical Physiology* (C. V. Mosby, 1956)), these characteristics assure a delivery to the tissues of 40% of the oxygen absorbed in the lungs by hemoglobin. The same is expected from a cell-free oxygen carrier with the same characteristics. The delivery of 25% of the oxygen bound by hemoglobin is generally considered enough to support life in humans in a resting state. This is the transport produced by an oxygen carrier with $P\frac{1}{2}=20$ mmHg and n=1.5. For this reason, acceptable hemoglobin-based oxygen carriers are those with $P\frac{1}{2}=20$ mmHg or higher, and n=1.5 or higher. This procedure can also be used, with modifications as necessary, to determine physiological competence in species other than humans.

As shown in the Table hereinafter, untreated stroma-free bovine hemoglobin exhibits a $P\frac{1}{2}$ of 32.66 mmHg and an n of 2.16, which per se would produce a delivery of 46% of the bound oxygen. However, this hemoglobin still dissociates into dimers and is readily eliminated in the urine after infusion (See Feola, M. et al, *Surg. Gyn. Obst.*, 157:399 (1983)). Therefore, it still must be cross-linked in order to stabilize its tetrameric structure so as to prolong its retention time.

E. Measurement of Retention Times In Vivo of Cross-Linked Hemoglobin (Intravascular Persistence)

Rabbits and rats are preferentially used for measurement of retention times in vivo of the cross-linked hemoglobin of the present invention because of their small size. After sedation and anesthetization, as necessary for maintaining the animals in a pain-free state, catheters are inserted into one carotid artery and one jugular vein. Blood is withdrawn from the artery while the liquid containing the cross-linked hemoglobin is infused through the vein, in an amount representing 40% of the blood volume. The plasma concentration of the cross-linked hemoglobin can then be measured in samples of blood withdrawn from the animal immediately after the infusion, 30 minutes later, and then hourly for 12 hours.

The following examples are further provided for illustrative purposes only and are in no way intended to limit the scope of the present invention.

EXAMPLE 1

Preparation of Stroma-Free Hemoglobin

One unit of outdated human blood obtained from a blood bank was poured into centrifuge containers and spun at 4° C., 3,000 rpm for 20 minutes to remove the plasma fraction. The pelleted erythrocytes were suspended and washed with 10 volumes of isotonic buffer (5 mM phosphate, 150 mM NaCl, pH 7.5) and centrifuged at 4° C., 3,000 rpm for 20 minutes. The supernatant was removed by aspiration. This procedure was repeated three times.

Alternatively, bovine blood was collected in ACD solution as above described, from the jugular vein of a cow of the Hereford breed, and the red cells were collected and washed in the same manner as described above for human blood. All of the procedures described below were applied to the resulting human and bovine blood.

The pelleted erythrocytes were then hemolyzed by addition of hypertonic buffer (5 mM phosphate, pH 7.5), to a final volume of 8 liters and filtered first through a 0.5 micrometer then through a 0.2 micrometer Millipore Pellicon cassette in order to separate the stroma from the stroma-free hemoglobin solution that filtered through the cassette. The stroma-free hemoglobin solution was concentrated, using a low molecular weight cut-off Millipore Pellicon cassette, cutting off at 10,000 MW, to a final volume producing a 10% w/v solution. The concentrated hemoglobin solution was then dialyzed using the same Pellicon cassette against 40 liters of 20 mM Tris buffer, pH 8.0.

In order to purify the hemoglobin component from the stroma-free hemolysate thus obtained, 1.0 g of the stroma-free hemoglobin was absorbed on an anionic resin (DEAE PW5, (Waters)) and chromatographed using a gradient formed by 20 mM Tris and 20 mM Tris, 500 mM NaCl, pH 8.0. An Altek high-performance liquid chromatography (HPLC) machine was employed for the chromatography. The major peak corresponding to pure hemoglobin was collected. The various minor fractions eluted before and after the major peak were discarded. The pure stroma-free hemoglobin was dialized 3 times against a 1:20 v/v of freshly prepared dionized-distilled water and stored at −80° C.

EXAMPLE 2

Preparation of Cross-Linked Hemoglobin Using MMSBA and Oxyhemoglobin

The cross-linking reaction was performed using a solution containing 60 mg/ml of purified stroma-free hemoglobin, obtained as in Example 1, in 0.01M Bis-tris buffer, pH 6.8. The hemoglobin solution was kept in a thermostatted container at 25° C. under a stream of humidified oxygen, humidified by the passage thereof through a bottle filled with water. The sample was constantly gently stirred. Then, 2 mg of MMSBA was added per ml of hemoglobin solution. The reaction was allowed to proceed for 30 minutes at 25° C. The reaction was stopped by forced filtration (1–2 p.s.i.) through a molecular sieve column of Sephadex 50 so as to remove any unwanted chemicals from the solutions, in particular, excess unreacted MMSBA.

EXAMPLE 3

Preparation of Cross-Linked Hemoglobin Using MMSBA and Deoxyhemoglobin

A 60 mg/ml solution of hemoglobin was prepared as described in Example 1. The solution was flushed with humidified nitrogen, obtained as described in Example 2 for humidified oxygen, in a closed vessel while the solution was gently stirred. Care was taken in order to avoid, during the flushing, the formation of bubbles which would promote the denaturation of the hemoglobin. Equilibration with nitrogen took about 15–20 minutes. When equilibration was reached, an oxygen-absorbing reagent, sodium dithionite, was added to a concentration of 1 mg/ml, so as to eliminate residual traces of oxygen. MMSBA was then added as in Example 2 via a syringe through the rubber cap of the closed vessel to the solution maintained under a stream of humidified nitrogen. After reacting for 30 minutes at 25° C., the reaction was stopped by forced filtration, using 1–2 p.s.i. nitrogen pressure, through a molecular sieve anaerobic Sephadex 50 column as described in Example 2. The cross-linked hemoglobin which was filtered from the column was collected in a vessel under a stream of humidified oxygen so as to completely reoxygenate the hemoglobin.

EXAMPLE 4

Purification of Cross-Linked Hemoglobins

As discussed above, it is preferred that the cross-linked hemoglobins of the present invention are obtained as a pure homogeneous component containing a single molecular species. Thus, a final purification step was conducted by chromatography on a DEAE PW5 column using an Altek HPLC machine. More specifically, the cross-linked hemoglobin equilibrated with 20 mM Tris, pH 8.0 and adsorbed on the column and eluted using a gradient formed by 20 mM Tris and 20 mM Tris, 500 mM NaCl, pH 8.0. Three peaks were obtained, wherein the first was a residual untreated hemoglobin, the second, which was the major fraction, represented the cross-linked hemoglobin, and the third represented a small component of overreacted hemoglobin.

The purity of the samples was assessed by microzone electrophoresis as discussed above. The pure cross-linked hemoglobin produced single sharp bands, with different mobility than untreated hemoglobin.

In SDS-urea electrophoresis (See Swank, R. T. et al, *Anal. Biochem.*, 39:462 (1971)) the purified fractions gave two bands corresponding to molecular weights of 32,000 and 16,000 Daltons, respectively. Optical scanning of the gel using a Joyce and Loeble microdensitometer indicated a relative proportion of 1:1 between the two bands, as expected from the cross-linking of only one pair of like subunits per molecule of tetrameric hemoglobin.

Sedimentation velocity experiments on the cross-linked hemoglobin gave sedimentation constants near 4.4 both in 0.05M phosphate buffer, pH 7.0, in the presence and absence of 1M NaCl. This demonstrated the absence of dissociation into dimers at high ionic strength.

EXAMPLE 5

Determination of Oxygen Affinities Of Various Cross-Linked Purified Hemoglobins

The cross-linked human hemoglobin purified as described in Example 4, was equilibrated with 0.15M Tris-HCl, pH 7.4 and its oxygen affinity was measured with a Hemoscan at 37° C. Similarly, bovine hemoglobin cross-linked and purified as described above in Examples 1–4 for human hemoglobin, was carried out and its oxygen affinity was also measured with a Hemoscan at 37° C. The results are shown in the following Table:

TABLE

Oxygen Affinity of Human and Bovine Hemoglobins Cross-linked with MMSBA

| Sample | P½ (mmHg) | n | % Delivery to Tissue of the Oxygen Bound Hemoglobin in the Lungs |
|---|---|---|---|
| Human red blood cells | 27.02 | 2.8 | 40 |
| Human stroma-free hemoglobin, (untreated) | 18.01 | 2.64 | 10 |
| Human stroma-free hemoglobin, (oxy-reacted) | 26.90 | 2.11 | 39 |
| Human stroma-free hemoglobin, (deoxy-reacted) | 26.95 | 2.41 | 39 |
| Bovine red blood cells | 33.01 | 2.3 | 52 |
| Bovine stroma-free hemoglobin, (untreated) | 32.66 | 2.16 | 46 |
| Bovine stroma-free hemoglobin, (oxy-reacted) | 38.17 | 1.52 | 40 |
| Bovine stroma-free hemoglobin, (deoxy-reacted) | 40.17 | 1.80 | 46 |

Note:
The last column in the Table shows values computed with the Hill equation (Wyman, J., Adv. Prot. Chem., 19:223 (1964) assuming that the partial pressure of oxygen is 100 mmHg in the lungs and 30 mmHg in the tissues.

In the Table above, P½ indicates the partial pressure of oxygen necessary for saturating hemoglobin at 50% (i.e., P½ measures the oxygen affinity). Also, the value n is the expression of oxygen-binding cooperativity, which in normal human red cells is very close to n=3.

As shown in the Table above, the cross-linked stroma-free hemoglobin obtained as described above had an oxygen affinity lower than that of the corresponding untreated stroma-free hemoglobin. In addition, all the cross-linked stroma-free human hemoglobins obtained had a value of n in the Hill plot near 2.3, demonstrating the persistance of a very good oxygen-binding cooperativity in the cross-linked hemoglobins.

Cross-linked bovine hemoglobins had a relatively low value of n, but it was still higher than 1.5.

As shown in the Table, and as above discussed, the oxygen binding characteristics of all of the cross-linked hemoglobins assured acceptable levels of oxygen delivery to tissues.

While the invention has been described in detail and with reference to specific embodiments thereof, it will be apparent to one skilled in the art that various changes and modifications can be made therein without departing from the spirit and scope thereof.

We claim:

1. Cross-linked stroma-free hemoglobin obtained by cross-linking stroma-free hemoglobin with at least one cross-linking reagent selected from the group consisting of compounds of the general formulae (I) and (II):

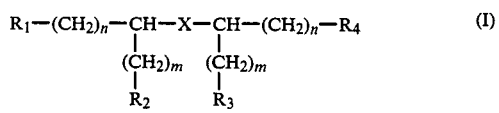

-continued

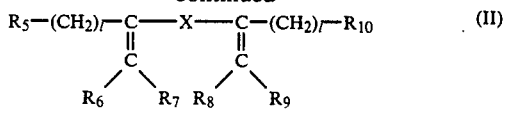

wherein one of $R_1$ or $R_2$ represents an electron-withdrawing atom or group, and the other of $R_1$ or $R_2$ represents a leaving atom or group or an electron-withdrawing group containing a leaving atom or group; one of $R_3$ or $R_4$ represents an electron-withdrawing atom or group, and the other of $R_3$ or $R_4$ represents a leaving atom or group or an electron-withdrawing group containing a leaving atom or group; $R_5$ and $R_{10}$, which may be the same or different, each represents an electron-withdrawing atom or group or an electron-withdrawing group containing a leaving atom or group; one of $R_6$ or $R_7$ represents a hydrogen atom, an alkyl group, an aryl group, or a heterocyclic group, and the other of $R_6$ or $R_7$ represents a leaving atom or group; one of $R_8$ or $R_9$ represents a hydrogen atom, an alkyl group, an aryl group or a heterocylic group, and the other of $R_8$ or $R_9$ represents a leaving atom or group; X represents a linking atom or group, n=0 to 4, m=0 to 4 and l=0 to 4.

2. The cross-linked stroma-free hemoglobin as claimed in claim 1, wherein the electron-withdrawing group represented by $R_1$, $R_2$, $R_3$, $R_4$, $R_5$ and $R_{10}$ is a member selected from the group consisting of CN, $NO_2$, halogen, $S(O)R_{11}$, $S(O_2)R_{11}$, $C(O)R_{11}$, wherein $R_{11}$ is selected from the group consisting of a hydrogen atom, a substituted or unsubstituted $C_1$-$C_{12}$ alkyl group, a substituted or unsubstituted mono- or bicyclic aryl group, and a substituted or unsubstituted heterocyclic group.

3. The cross-linked stroma-free hemoglobin as claimed in claim 2, wherein said substituents on said alkyl group, aryl group, and heterocyclic group are selected from the group consisting of a halogen atom, CN, a $C_1$-$C_{12}$ alkyl group, a substituted or unsubstituted phenyl group, $NO_2$, OH, and a $C_1$-$C_{12}$ alkoxy group.

4. The cross-linked stroma-free hemoglobin as claimed in claim 2, wherein said heterocyclic group is selected from the group consisting of substituted or unsubstituted imidazolyl and substituted or unsubstituted pyrazinyl.

5. The cross-linked stroma-free hemoglobin as claimed in claim 1, wherein $R_1$, $R_2$, $R_3$, $R_4$, $R_5$, and $R_{10}$ are selected from the group consisting of CN and $SO_2R_{11}$.

6. The cross-linked stroma-free hemoglobin as claimed in claim 1, wherein the electron-withdrawing group containing a leaving group represented by $R_1$, $R_2$, $R_3$, $R_4$, $R_5$ and $R_{10}$ is a member selected from the group consisting of $R_{12}P(O)OR_{12}$, $P(O)(OR_{12})_2$, OP(O)(OR_{12})_2$ and $CO_2R_{12}$, wherein $R_{12}$ is selected from the group consisting of a hydrogen atom, a substituted or unsubstituted $C_1$-$C_{12}$ alkyl group, a substituted or unsubstituted mono- or bicyclic aryl group, a substituted or unsubstituted heterocyclic group and a halogen atom and $P(O)(R_{13})_2$, $S(O)R_{13}$, $S(O_2)R_{13}$ and $C(O)R_{13}$, wherein $R_{13}$ is a halogen atom.

7. The cross-linked stroma-free hemoglobin as claimed in claim 1, wherein the group other than a leaving group represented by $R_6$, $R_7$, $R_8$ and $R_9$ is selected from the group consisting of a hydrogen atom, a $C_1$-$C_{12}$ alkyl group, an aryl group, and a heterocyclic group.

8. The cross-linked stroma-free hemoglobin as claimed in claim 7, wherein $R_6$, $R_7$, $R_8$ and $R_9$ are selected from the group consisting of $C_2H_5$, a phenyl group, or an imidazolyl group.

9. The cross-linked stroma-free hemoglobin as claimed in claim 1, wherein the leaving group represented by $R_1$, $R_2$, $R_3$, $R_4$, $R_6$, $R_7$, $R_8$ and $R_9$ is selected from the group consisting of a halogen atom and $OR_{11}$, wherein $R_{11}$ is selected from the group consisting of a hydrogen atom, a substituted or unsubstituted $C_1$–$C_{12}$ alkyl group, a substituted or unsubstituted mono- or bicyclic aryl group and a substituted or unsubstituted heterocyclic group.

10. The cross-linked stroma-free hemoglobin as claimed in claim 9, wherein $R_7$ and $R_9$ are selected from the group consisting of $CH_3$, $C_2H_5$ and $CH_2C_6H_5$.

11. The cross-linked stroma-free hemoglobin as claimed in claim 1, wherein X is selected from the group consisting of $SO_2$, SO, $P(O)(OR_{11})$, CO, Se, Te and Sr, wherein $R_{11}$ is selected from the group consisting of a hydrogen atom, a substituted or unsubstituted $C_1$–$C_{12}$ alkyl group, a substituted or unsubstituted mono- or bicyclic aryl group and a substituted or unsubstituted heterocyclic group.

12. The cross-linked stroma-free hemoglobin as claimed in claim 11, wherein X is selected from the group consisting of $SO_2$, SO, $P(O)(OR_{11})$ and CO, wherein $R_{11}$ is as defined in claim 11.

13. The cross-linked stroma-free hemoglobin as claimed in claim 1, wherein n=0 to 2, n=0 to 2, and l=0 to 2.

14. The cross-linked stroma-free hemoglobin as claimed in claim 1, wherein said reagent is selected from the group consisting of ethyl-2,2'-sulfonyl-bis-cyanoacetate, diethyl-2,2'-sulfonyl-bis-malonate, ethyl-2,2'-sulfonyl-2,2'-benzene sulfonyl-bis-acetate, 2,2'-sulfonyl-2,2'-imidazole-N-sulfonyl-bis-acetonitrile, methyl 2,2'-sulfonyl-bis-cyanoacetate, 2,2'-methoxymethylene-2,2'-sulfonyl-bis-acetonitrile and dimethyl 2,2'-methoxyphosphinylidene-2-2'-methoxymethylene-bis-methanephosphonate.

15. The cross-linked stroma-free hemoglobin as claimed in claim 1, wherein said stroma-free hemoglobin is selected from the group consisting of human, equine, porcine, ovine, bovine, simian and fish hemoglobin.

16. The cross-linked stroma-free hemoglobin as claimed in claim 1, wherein said stroma-free hemoglobin is bovine hemoglobin.

17. The cross-linked stroma-free hemoglobin as claimed in claim 1, wherein said stroma-free hemoglobin is human hemoglobin.

18. The cross-linked stroma-free hemoglobin as claimed in claim 1, wherein said cross-linking is carried out in the presence of oxygen.

19. The cross-linked stroma-free hemoglobin as claimed in claim 1, wherein said cross-linking is carried out in the absence of oxygen.

20. A method of producing cross-linked stroma-free hemoglobin, comprising:
(a) cross-linking stroma-free hemoglobin with at least one cross-linking reagent selected from the group consisting of compounds of the general formulae (I) and (II):

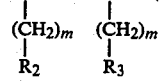

wherein one of $R_1$ or $R_2$ represents an electron-withdrawing atom or group, and the other of $R_1$ or $R_2$ represents a leaving atom or group or an electron-withdrawing group containing a leaving atom or group; one of $R_3$ or $R_4$ represents an electron-withdrawing atom or group, and the other of $R_3$ or $R_4$ represents a leaving atom or group or an electron-withdrawing group containing a leaving atom or group; $R_5$ and $R_{10}$, which may be the same or different, each represents an electron-withdrawing atom or group or an electron-withdrawing group containing a leaving atom or group; one of $R_6$ or $R_7$ represents a hydrogen atom, an alkyl group, an aryl group, or a heterocyclic group, and the other of $R_6$ or $R_7$ represents a leaving atom or group; one of $R_8$ or $R_9$ represents a hydrogen atom, an alkyl group, an aryl group or a heterocyclic group, and the other of $R_8$ or $R_9$ represents a leaving atom or group; X represents a linking atom or group, n=0 to 4, m=0 to 4 and l=0 to 4; and
(b) purifying the resulting cross-linked hemoglobin.

21. The method of producing cross-linked stroma-free hemoglobin as claimed in claim 20, wherein the electron-withdrawing group represented by $R_1$, $R_2$, $R_3$, $R_4$, $R_5$ and $R_{10}$ is a member selected from the group consisting of CN, $NO_2$, halogen, $S(O)R_{11}$, $S(O_2)R_{11}$, $C(O)R_{11}$, wherein $R_{11}$ is selected from the group consisting of a hydrogen atom, a substituted or unsubstituted $C_1$–$C_{12}$ alkyl group, a substituted or unsubstituted mono- or bicyclic aryl group, and a substituted or unsubstituted heterocyclic group.

22. The method of producing cross-linked stroma-free hemoglobin as claimed in claim 21, wherein said substituents on said alkyl group, aryl group, and heterocyclic group are selected from the group consisting of a halogen atom, CN, a $C_1$–$C_{12}$ alkyl group, a substituted or unsubstituted phenyl group, $NO_2$, OH, and a $C_1$–$C_{12}$ alkoxy group.

23. The mthod of producing cross-linked stroma-free hemoglobin as claimed in claim 21, wherein said heterocyclic group is selected from the group consisting of substituted or unsubstituted imidazolyl and substituted or unsubstituted pyrazinyl.

24. The method of producing cross-linked stroma-free hemoglobin as claimed in claim 21, wherein $R_1$, $R_2$, $R_3$, $R_4$, $R_5$, and $R_{10}$ are selected from the group consisting of CN and $SO_2R_{11}$.

25. The method of producing cross-linked stroma-free hemoglobin as claimed in claim 20, wherein the electron-withdrawing group containing a leaving group represented by $R_1$, $R_2$, $R_3$, $R_4$, $R_5$ and $R_{10}$ is a member selected from the group consisting of $R_{12}P(O)OR_{12}$, $P(O)(OR_{12})_2$, $OP(O)(OR_{12})_2$, and $CO_2R_{12}$, wherein $R_{12}$ is selected from the group consisting of a hydrogen atom, a substituted or unsubstituted $C_1$–$C_{12}$ alkyl group, a substituted or unsubstituted mono- or bicyclic aryl group, a substituted or unsubstituted heterocyclic group and a halogen atom and $P(O)(R_{13})_2$, $S(O)R_{13}$, $S(O_2)R_{13}$ and $C(O)R_{13}$, wherein $R_{13}$ is a halogen atom.

26. The method of producing cross-linked stroma-free hemoglobin as claimed in claim 20, wherein the group other than a leaving group represented by $R_6$, $R_7$, $R_8$ and $R_9$ is selected from the group consisting of a hydrogen atom, a $C_1$–$C_{12}$ alkyl group, an aryl group, and a heterocyclic group.

27. The method of producing cross-linked stroma-free hemoglobin as claimed in claim 26, wherein $R_6$, $R_7$, $R_8$ and $R_9$ are selected from the group consisting of $C_2H_5$, a phenyl group, or an imidazolyl group.

28. The method of producing cross-linked stroma-free hemoglobin as claimed in claim 20, wherein the leaving group represented by $R_1$, $R_2$, $R_3$, $R_4$, $R_6$, $R_7$, $R_8$ and $R_9$ is selected from the group consisting of a halogen atom and $OR_{11}$, wherein $R_{11}$ is selected from the group consisting of a hydrogen atom, a substituted or unsubstituted $C_1$–$C_{12}$ alkyl group, a substituted or unsubstituted mono- or bicyclic aryl group and a substituted or unsubstituted heterocyclic group.

29. The method of producing cross-linked stroma-free hemoglobin as claimed in claim 28, wherein $R_{11}$ is selected from the group consisting of $CH_3$, $C_2H_5$, $CH_2C_6H_5$, and $C_6H_5$.

30. The method of producing cross-linked stroma-free hemoglobin as claimed in claim 20, wherein X is selected from the group consisting of $SO_2$, SO, $P(O)(OR_{11})$, CO, Se, Te and Sr, wherein $R_{11}$ is selected from the group consisting of a hydrogen atom, a substituted or unsubstituted $C_1$–$C_{12}$ alkyl group, a substituted or unsubstituted mono- or bicyclic aryl group and a substituted or unsubstituted heterocyclic group.

31. The method of producing cross-linked stroma-free hemoglobin as claimed in claim 30, wherein X is selected from the group consisting of $SO_2$, SO, $P(O)(OR_{11})$ and CO, wherein $R_{11}$ is as defined above.

32. The method of producing cross-linked stroma-free hemoglobin as claimed in claim 20, wherein n=0 to 2, n=0 to 2, and l=0 to 2.

33. The method of producing cross-linked stroma-free hemoglobin as claimed in claim 20, wherein said reagent is selected from the group consisting of ethyl-2,2'-sulfonyl-bis-cyanoacetate, diethyl-2,2'-sulfonyl-bis-malonate, ethyl-2,2'-sulfonyl-2,2'-benzene sulfonyl-bis-acetate, 2,2'-sulfonyl-2,2'-imidazole-N-sulfonyl-bis-acetonitrile, methyl 2,2'-sulfonyl-bis-cyanoacetate, 2,2'-methoxymethylene-2,2'-sulfonyl-bis-acetonitrile and dimethyl 2,2'-methoxyphosphinylidene-2-2'-methoxymethylene-bis-methanephosphonate.

34. The method of producing cross-linked stroma-free hemoglobin as claimed in claim 20, wherein said stroma-free hemoglobin is selected from the group consisting of human, equine, porcine, ovine, bovine, simian and fish hemoglobin.

35. The method of producing cross-linked stroma-free hemoglobin as claimed in claim 20, wherein said stroma-free hemoglobin is bovine hemoglobin.

36. The method of producing cross-linked stroma-free hemoglobin as claimed in claim 20, wherein said stroma-free hemoglobin is human hemoglobin.

37. The method of producing cross-linked stroma-free hemoglobin as claimed in claim 20, wherein said cross-linking is carried out in the presence of oxygen.

38. The method of producing cross-linked stroma-free hemoglobin as claimed in claim 20, wherein said cross-linking is carried out in the absence of oxygen.

39. The method of producing cross-linked hemoglobin as claimed in claim 20, wherein said cross-linking is carried out at about 10° C. to 37° C.

40. The method of producing cross-linked hemoglobin as claimed in claim 39 wherein said cross-linking is carried out at about 25° C. to 30° C.

41. The method of producing cross-linked hemoglobin as claimed in claim 20, wherein the molar ratio of said reagent to said hemoglobin is 1:1 to 1:10.

42. The method of producing cross-linked hemoglobin as claimed in claim 41, wherein the molar ratio of said reagent to said hemoglobin is 1:2 to 1:6.

* * * * *